(12) United States Patent
Gagne

(10) Patent No.: US 10,914,415 B2
(45) Date of Patent: Feb. 9, 2021

(54) FLUID PLUG FOR STERILE PROCESSES AND METHODS OF USING THE SAME

(71) Applicant: Repligen Corporation, Waltham, MA (US)

(72) Inventor: Michael C. Gagne, Carson City, NV (US)

(73) Assignee: Repligen Corporation, Waltham, MA (US)

( * ) Notice: Subject to any disclaimer, the term of this patent is extended or adjusted under 35 U.S.C. 154(b) by 193 days.

(21) Appl. No.: 15/749,773

(22) PCT Filed: Aug. 3, 2016

(86) PCT No.: PCT/US2016/045414
§ 371 (c)(1),
(2) Date: Feb. 1, 2018

(87) PCT Pub. No.: WO2017/024068
PCT Pub. Date: Feb. 9, 2017

(65) Prior Publication Data
US 2020/0088337 A1    Mar. 19, 2020

Related U.S. Application Data

(60) Provisional application No. 62/201,044, filed on Aug. 4, 2015.

(51) Int. Cl.
*F16L 55/11* (2006.01)
*A61L 2/07* (2006.01)
(Continued)

(52) U.S. Cl.
CPC ............ *F16L 55/1141* (2013.01); *A61L 2/07* (2013.01); *A61L 2/081* (2013.01); *A61L 2/202* (2013.01);
(Continued)

(58) Field of Classification Search
CPC ........ F16L 55/11; F16L 55/13; F16L 55/1141; A61M 16/0816; A61M 16/0833;
(Continued)

(56) References Cited

U.S. PATENT DOCUMENTS 408,364 A    8/1889  Traut
4,282,863 A  8/1981  Beigler et al.
(Continued)

OTHER PUBLICATIONS

PCT International Search Report for PCT/US2016/045414, Applicant: Alphinity, LLC, Form PCT/ISA/210 and 220, dated Jan. 27, 2017 (6pages).
(Continued)

*Primary Examiner* — Timothy L Maust
(74) *Attorney, Agent, or Firm* — Kacvinsky Daisak Bluni PLC

(57) ABSTRACT

A fluid plug for use with sterile processes such as the manufacture or production of pharmaceuticals and biologics is disclosed. The fluid plug is made of a material or materials that will tolerate sterilizing processes such as gamma irradiation. The fluid plug is used to selectively plug the ends of flexible polymer conduits that may be connected to fluids, reagents, or products used or generated as part of the manufacturing process. Also disclosed is the use of the plugs in combination with a series of valves in a block-and-bleed arrangement to enable the sterile transfer and connection of fluids, reagents, or products within a process flow.

7 Claims, 6 Drawing Sheets

(51) Int. Cl.
*A61L 2/08* (2006.01)
*A61L 2/20* (2006.01)

(52) U.S. Cl.
CPC ..... *A61L 2202/181* (2013.01); *A61L 2202/23* (2013.01)

(58) Field of Classification Search
CPC ...... A61M 16/0875; A61L 2/07; A61L 2/081; A61L 2/202
See application file for complete search history.

(56) References Cited

U.S. PATENT DOCUMENTS

| | | |
|---|---|---|
| 4,407,660 A | 10/1983 | Nevens et al. |
| 2015/0118743 A1 | 4/2015 | Hanamura et al. |

OTHER PUBLICATIONS

PCT Written Opinion of the International Search Authority for PCT/US2016/045414, Applicant: Alphinity, LLC, Form PCT/ISA/237, dated Jan. 27, 2017 (6pages).

PCT International Preliminary Report on Patentability (Chapter I of the Patent Cooperation Treaty) for PCT/US2016/045414, Applicant: Alphinity, LLC, Form PCT/IB/326 and 373, dated Feb. 15, 2018 (8pages).

US 10,914,415 B2

FLUID PLUG FOR STERILE PROCESSES AND METHODS OF USING THE SAME

RELATED APPLICATION

This Application is a U.S. National Stage filing under 35 U.S.C. § 371 of International Application No. PCT/US2016/045414, filed Aug. 3, 2016, which claims priority to U.S. Provisional Patent Application No. 62/201,044 filed on Aug. 4, 2015, which is hereby incorporated by reference. Priority is claimed pursuant to 35 U.S.C. §§ 119, 371 and any other applicable statute.

FIELD OF THE INVENTION

The field of the invention generally relates to plugs that are used in connection with connectors, valves, or interfaces used by pharmaceutical and biological applications or other hygienic process industries.

BACKGROUND

Many commercial products are produced using chemical as well as biological processes. Pharmaceuticals, for example, are produced in commercial quantities using scaled-up reactors and other equipment. So-called biologics are drugs or other compounds that are produced or isolated from living entities such as cells or tissue. Biologics can be composed of proteins, nucleic acids, or complex combinations of these substances. They may even include living entities such as cells. In order to produce biologics on a commercial scale, sophisticated and expensive equipment is needed. In both pharmaceutical and biologics, for example, various processes need to occur before the final product is obtained. For example, in the case of biologics, cells may be grown in a growth chamber or the like and nutrients may need to be carefully modulated into the growth chamber. Waste products produced by cells may also have to be removed on a controlled basis from the fermentation chamber. As another example, biologic products produced by living cells or other organisms may need to be extracted and concentrated. This process may involve a variety of filtration and separation techniques.

Because there are a number of individual processes required to be produce the final product, various reactants, solutions, and washes are often pumped or otherwise transported to various subsystems using conduits and associated valves. These systems may be quite cumbersome and organizationally complex due to the large numbers of conduits, valves, sensors, and the like that may be needed in such systems. Not only are these systems visually complex (e.g., resembling spaghetti) they also include many components that are required to be sterilized between uses to avoid cross-contamination issues. Indeed, the case of drug and biologic preparation, the Federal Food and Drug Administration (FDA) is becoming increasingly strict on cleaning, sterilization or bio-burden reduction procedures that are required for drug and pharmaceutical preparations. This is particularly of a concern because many of these products are produced in batches which would require repeated cleaning, sterilization or bio-burden reduction activities on a variety of components.

During the manufacturing process of pharmaceuticals and biologics sterile solutions and reagents are used. These sterile solutions and reagents need to be integrated into the manufacturing process in a manner that maintains the sterile nature of the reagents without any chance of introducing contaminants into the system when the reagents are coupled to the larger production system. There is a need for devices and systems that can be used to for the preparation and use of such solutions and reagents that maintains their sterile integrity or can otherwise be subject to cleaning or disinfectant operations to sterilize the same. Preferably these devices and systems and be used with conventional sterilization modalities such gamma irradiation.

SUMMARY

A fluid plug for use with sterile processes such as the manufacture or production of pharmaceuticals and/or biologics, and food or dairy applications is disclosed. The fluid plug is made of materials that will tolerate sterilizing processes such as gamma irradiation. The fluid plug is used to selectively plug the ends of flexible polymer conduits that may be connected to fluids, reagents, or products used or generated as part of the manufacturing process. Also disclosed is the use of the plugs in combination with a series of valves in a block-and-bleed arrangement to enable the sterile transfer and connection of fluids, reagents, or products within a process flow.

In one embodiment, a sterile fluid system is disclosed that includes a container for holding fluid therein and a flexible polymer conduit having first and second ends, the flexible polymer conduit coupled to the container at the first end. A removable plug is configured to insert into the second end of the flexible polymer conduit. The removable plug includes a cap, a shank portion extending from the cap, a flexible ring disposed along a portion of the shank, and a lever mounted on the cap and configured to shorten the shank upon actuation, wherein actuation of the lever causes radial expansion of the flexible ring and forms a fluidic seal with an interior surface of the flexible polymer conduit.

In another embodiment, a removable plug that is configured to insert into an end of a flexible polymer conduit is disclosed. The removable plug includes a cap, a shank portion extending from the cap, a flexible ring disposed along a portion of the shank, and a lever mounted on the cap and configured to shorten the shank upon actuation, wherein actuation of the lever causes radial expansion of the flexible ring and forms a fluidic seal with an interior surface of the flexible polymer conduit, wherein the removable plug is formed from materials that tolerate gamma irradiation.

In still another embodiment, a method of connecting a fluid container to a secondary conduit in a sterile manner includes sterilizing the fluid container and a first conduit connected to the fluid container, wherein the first conduit includes a main conduit and branch conduit and wherein an end of the branch conduit and an end of the main conduit each contain a removable plug therein. A first valve body is secured around the main conduit and the branch conduit of the first conduit, wherein the first valve body includes a first valve for the main conduit and second valve for the branch conduit. The first valve of the first valve body is then closed along with the second valve of the first valve body. The plugs are removed from the branch conduit and main conduit of the first conduit. A second valve body is secured around a secondary conduit, the secondary conduit having a main conduit and a branch conduit, wherein the second valve body includes a first valve for the main conduit and second valve for the branch conduit of the secondary conduit. The output of the main conduit of the first conduit is fluidically coupled (e.g., directly or indirectly using another conduit or the like) to the main conduit of the secondary conduit. The second valve of the first valve body is opened along with second valve of the second valve body. A sterilant is then flowed through a fluid pathway connecting between the branch channel of the first conduit and the branch channel of the secondary conduit. The second valve of the first valve body and the second valve of the second valve body are then closed. The first valve of the first valve body and the first valve of the second valve body are then opened to permit flow.

DETAILED DESCRIPTION OF THE ILLUSTRATED EMBODIMENTS

Figure 1A:
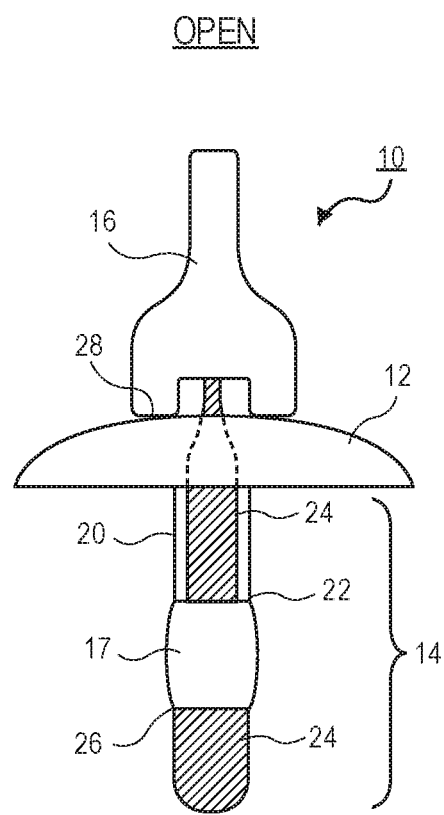
FIG. 1A illustrates a plug according to one embodiment with the plug in an open state.
Figure 1B:
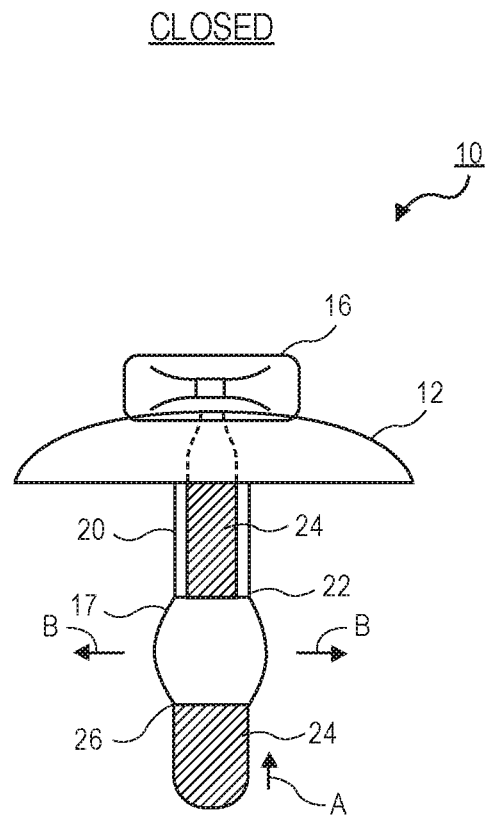
FIG. 1B illustrates the plug of FIG. 1A with the plug in the closed state.
Figure 2:
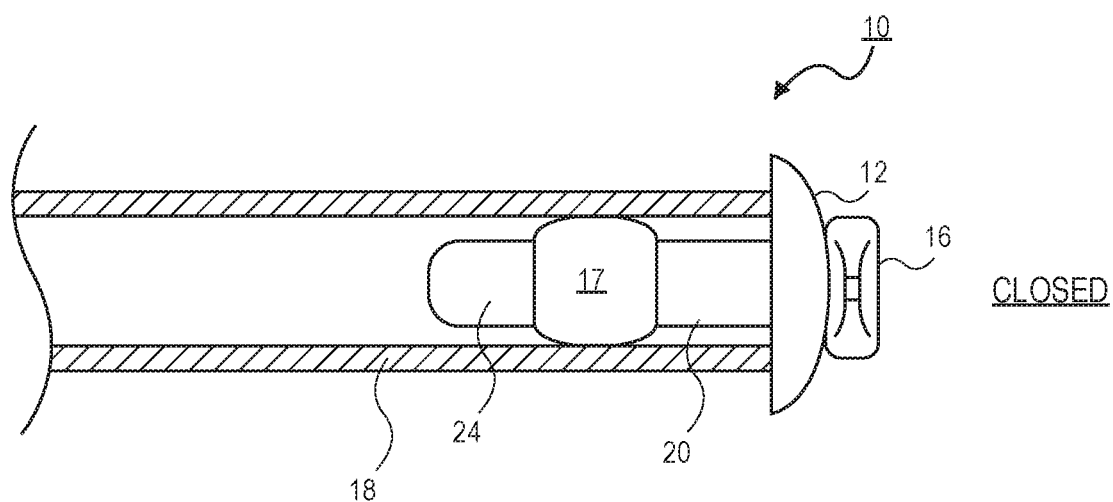
FIG. 2 illustrates a cross-sectional view of a removable plug inserted into an end of a conduit with the lever actuated with the plug in a closed state.

FIGS. 1A and 1B illustrate a plug 10 according to one embodiment. The plug 10 includes a cap 12 and an elongate shank portion 14 that extends generally perpendicular with respect to the cap 12. A lever 16 is disposed atop the cap 12 and as explained herein, is used to adjust length of the shank portion 14 during actuation to cause a ring 17 made from a flexible material to expand outward (i.e., radially with respect to long axis of shank portion 14). The outward expansion of the ring 17 is caused by the compression of the ring 17 along the direction of the shank portion 14 during actuation of the lever 16 as described below. When placed in an end of a conduit 18, the expansion of the ring 17 in the outward direction causes the ring 17 to contact an inner surface of a conduit 18 (as seen in FIG. 2) in which the plug 10 is placed to form a fluidic seal and prevent the passage of fluid. Conversely, after the plug 10 inserted into the conduit 18 and secured to an inner surface, the lever 16 can be actuated in the reverse direction to cause ring 17 to contract inwardly and away from the inner surface of the conduit 18. The plug 10 can now be removed from the conduit 18. Importantly, this provides for the damage-free removal of the plug 10 from the conduit 18. This is unlike, for example, barbed ends that, when removed, may affect the shape and size of the internal surface of the conduit 18. The plugs 10 described herein can be used to make selective (sealing) contact with the inner surface of the conduit 18 without any damage.

The elongate shank portion 14 includes an extension or portion 20 that projects from the cap 12 and is fixed relative to the cap 12. The extension 20 includes a flange or abutment 22 at the end that contacts with or is secured to one end of the ring 17. A moveable shaft 24 is located inside the extension 20 and extends through the interior of the ring 17 and terminates or otherwise connects to a containment flange or abutment 26 that is located on and extends from an opposing side of the ring 17 (e.g., this forms a moveable portion of the shank portion 14). The ring 17 may be bonded or secured to the containment flange or abutment 26. In this regard, the ring 17 is sandwiched between the flange/abutment 22 of the extension 20 and the moveable containment flange/abutment 26 on the shaft 24. Still referring to FIG. 1A, the moveable shaft 24 extends through the cap 12 and is connected to the lever 16. Note that a separate linkage or hinge may be used between the lever 16 and the shaft 24 instead of a direct connection. The lever 16 includes a lower cam surface 28 that contacts the upper surface of the cap 12. The lower cam surface 28 may be in the configuration as a saddle as illustrated in FIGS. 1A and 1B. Rotation (e.g., actuation) of the lever 16 as seen in FIG. 1B causes the lever to rotate about the lower cam surface 28 and the shaft 24 is pulled upward in the direction of arrow A. The shank portion 14 thus shortens in length and the containment flange/abutment 26 compresses the ring 17 against the stationary flange/abutment 22 and causes the ring 17 to bulge outward in the radial direction of arrows B of FIG. 1B. The outward bulging of the ring 17 will cause the exterior surface of the ring 17 to contact an inner surface of the conduit 18 (FIG. 2) in which the plug 10 is placed to form a fluidic seal. Sufficient frictional contact is made between the bulging ring 17 and the inner surface of the conduit 18 such that fluid cannot pass to the other side of the ring 17 thereby making a fluidic seal.

The components of the plug 10 should be made from materials that are suitable for sterilization processes typically used in biological and pharmaceutical applications including but not limited to irradiation (i.e., gamma irradiation). The components of the plug may be made from polymer materials such as silicone. Materials may also include standard thermoplastics and polyolefins such as polyethylene (PE) and polypropylene (PP) or a hard plastic such as polyetherimide (PEI) such as ULTEM resins, polycarbonate, and polysulfones (PSU). The ring 17 is preferably formed from a deformable polymer material such as, for example, rubber or silicone.

Figure 3A:
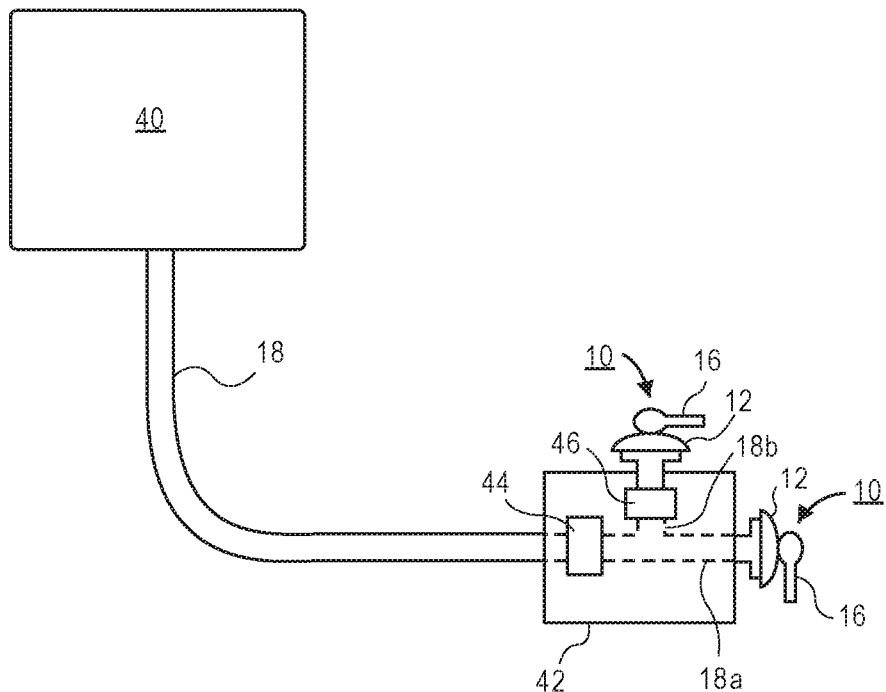
FIG. 3A illustrates a container (e.g., bag) connected to a conduit that terminates in a valve body having two plugs inserted into the conduit (plugs inserted at end of main and end of branch conduit).
Figure 3B:
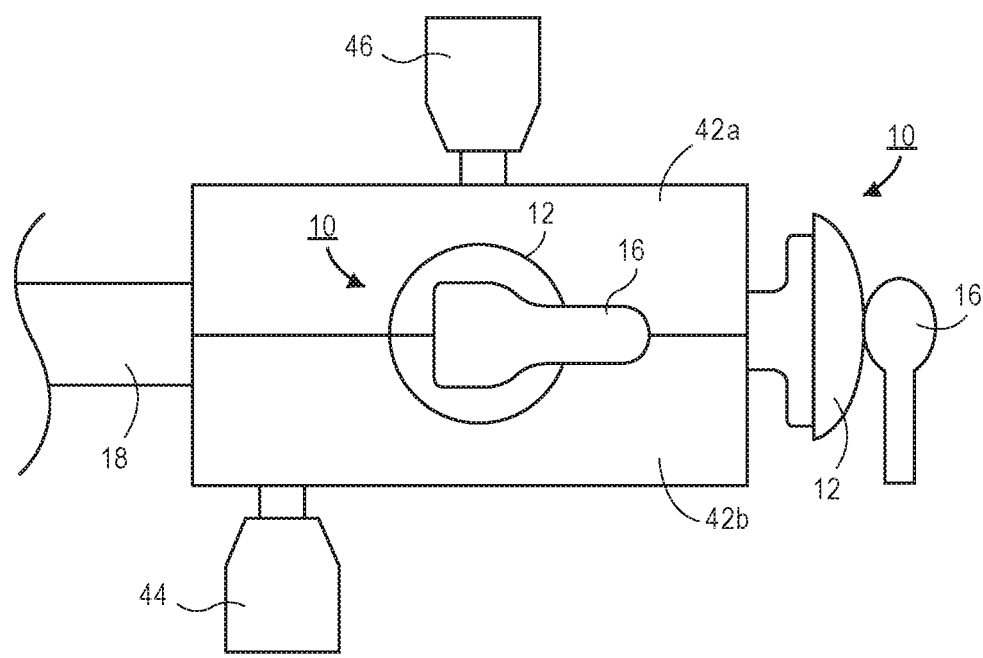
FIG. 3B illustrates a side view of the valve body according to one embodiment. In this embodiment, the conduit is encapsulated by a two-piece valve body. The valve body has two valves (one for main conduit and one for branch conduit). Plugs are illustrated inserted into, respectively, the ends of the main conduit and branch conduit.
Figure 5:
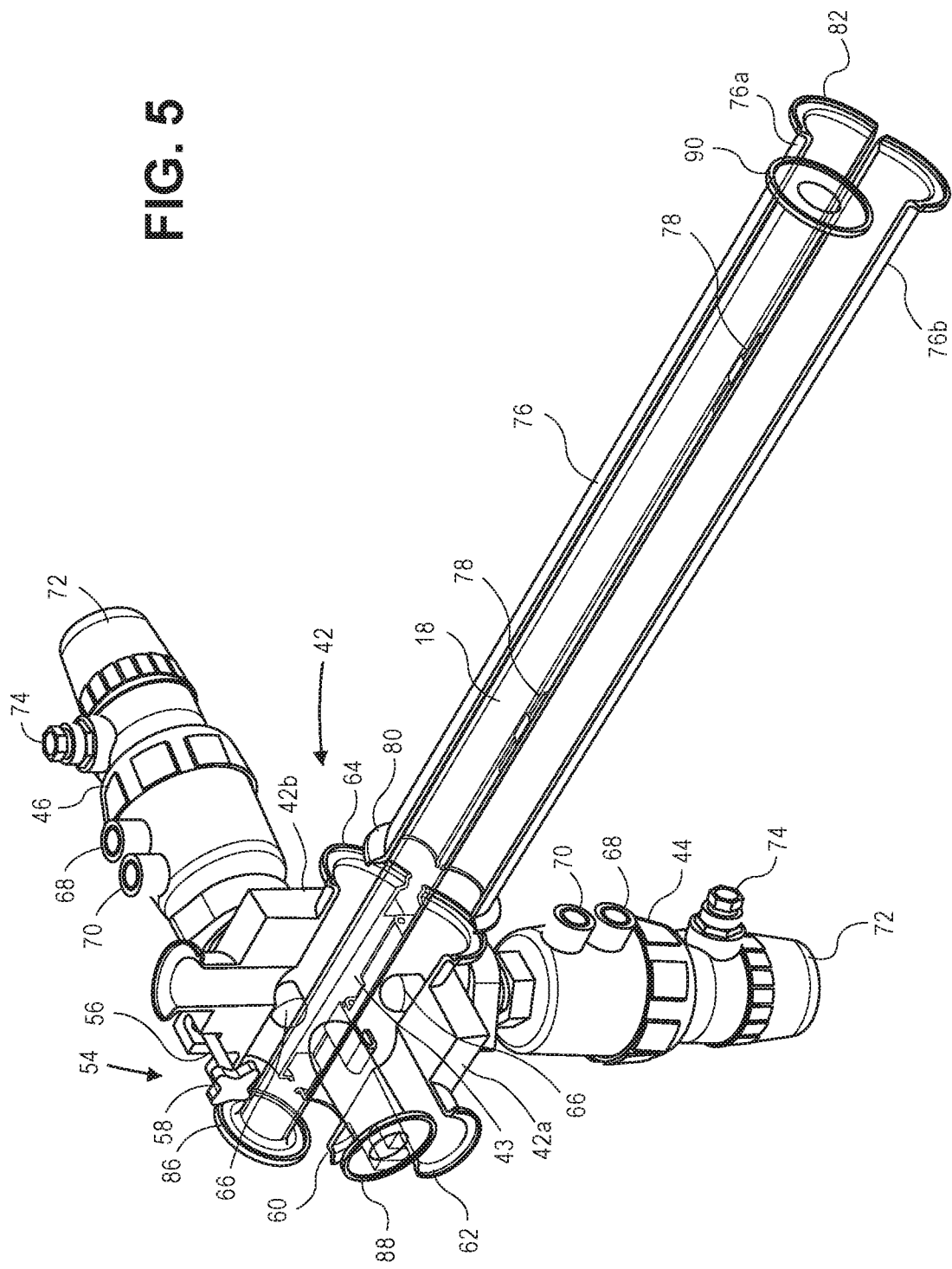
FIG. 5 illustrates one illustrative example of a two-piece valve body as well as an associated exoskeleton or external jacket that is used to cover a conduit that is placed within the two-piece valve body.

FIGS. 3A and 3B illustrate the use of plugs 10 according to one embodiment. In this embodiment, a bag, container, or the like 40 is illustrated that contains fluid therein. The fluid may contain reagents, products, or other process components in fluidic form. The bag 40 is connected to a conduit 18 that includes at one end a valve body 42. In this embodiment, the valve body 42 includes two valves 44, 46. The conduit 18 includes a main conduit 18a and a branch conduit 18b. A first valve 44 is used to control flow within the main conduit 18a while the second valve 46 is used to control flow within the branch conduit 18. The valve body 42 may include any number of types of valve bodies. For example, according to one embodiment and as explained in further detail below, the valve body 42 includes an exoskeleton type valve body in which the conduit 18 is flexible (e.g., silicone) and contained within a hardened jacket or housing that may be opened and closed (e.g., valve housing has first and second hinged halves 42a and 42b as seen in FIG. 3B that can be opened and closed around the conduit 18; see also FIG. 5). The actual valves 44, 46 used in the valve body 42 may be manually controlled valves or automatically controlled valves (e.g., pneumatic-based or solenoid based valves). The valves 44, 46 are pinch valves in that actuation of the valve 44, 46 causes an actuator element to pinch (or not pinch) the flexible conduit 18. The valve 44, 46 is thus able to stop flow by pinching the flexible conduit 18 or, conversely, allow flow by not pinching the flexible conduit 18. FIG. 5 illustrates two such actuator elements 66 that are used to pinch the flexible conduit 18.

Referring to FIGS. 3A and 3B, two plugs 10 are inserted into terminal ends of the conduit 18. One plug 10 is used to close the main conduit 18a while another plug 10 is used to close the branch conduit 18b. In one aspect of the invention, the bag or container 40, conduit 18, and plugs 10 are subject to irradiation such as, for example, gamma irradiation. For example, without the valve body 42 being attached, the entire apparatus is placed in gamma irradiation device and irradiated to ensure sterility. After being subject to irradiation, the valve body 42 may be opened and the conduits 18a, 18b placed within the respective housing halves 42a, 42b and the valve body 42 may be closed about the periphery of the conduits 18a, 18b. The valve body 42 may include one or more fasteners such as the threaded latch 56 of FIG. 5 to close the respective halves 42a, 42b (The plugs 10 maintain the sterility of the system after irradiation. FIG. 3B illustrates the valve body halves 42a, 42b closed around the conduits 18a, 18b.

Figure 4A:
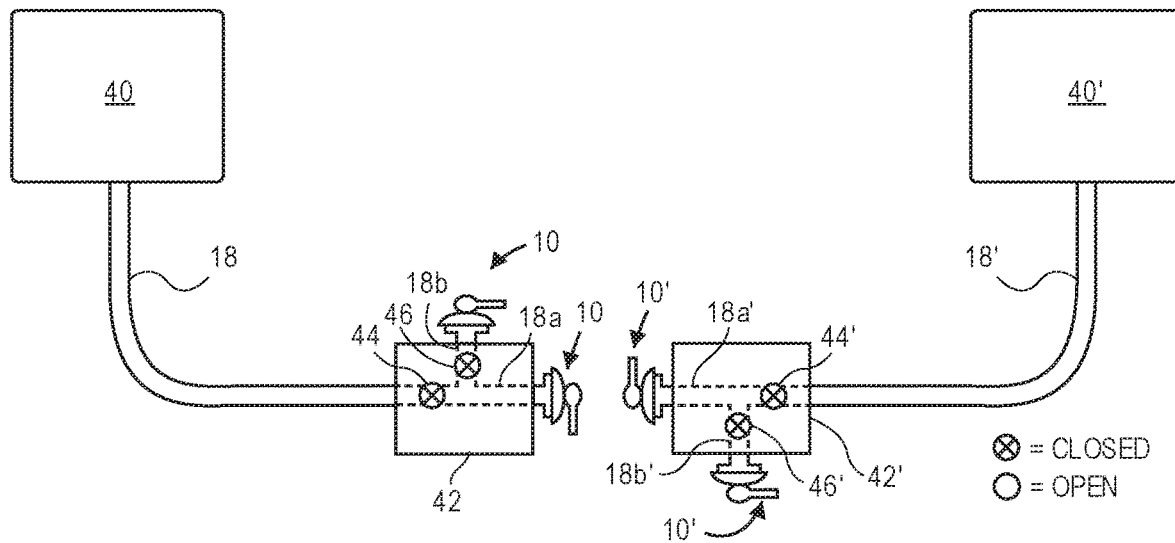
FIGS. 4A-4E illustrate one method of using the removable plugs in a block-and-bleed arrangement to aseptically connect or transfer a fluid-containing container or the like to another conduit. The other conduit may be connected to another source of fluid or the conduit may be part of a biological or pharmaceutical manufacturing process.
Figure 4B:
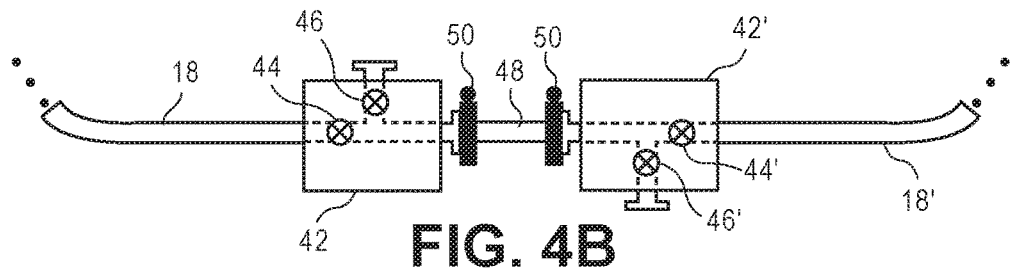

FIGS. 4A-4E illustrate how the plugs 10, 10' are used according to another embodiment. In this embodiment, the plugs 10, 10' are used to, for example, to transport and connect different process aspects in a sterile or aseptic manner. With reference to FIG. 4A, a bag or other container 40 is connected via a conduit 18 to a valve body 42 as previously described in FIGS. 3A and 3B. In this particular example, the main conduit 18a of the valve body 42 is connected to the main conduit 18' (e.g., receiving conduit) of another bag or container 40' that has its own valve body 42' using an optional conduit segment 48. As seen in FIG. 4A, plugs 10, 10' are used to close the main conduits 18a, 18a' and the branch conduits 18b, 18b' in both conduit lines 18, 18'. This maintains sterile or aseptic conditions within each respective system. Next, as seen in FIG. 4B, the valves 44, 46 and 44', 46' of the respective valve bodies 42, 42' are closed (if not already closed) and the plugs 10, 10' are removed. The respective main conduits 18a, 18a' are connected to one another using a conduit segment 48. The conduit segment 48 may be connected to respective ends of the main conduits 18a, 18a' using a clamp 50 or the like. Note that the conduit segment 48 may be jacketed with a rigid housing or exoskeleton in some embodiments as is illustrated in FIG. 5 (e.g., where the fluid is pressurized).

Figure 4C:
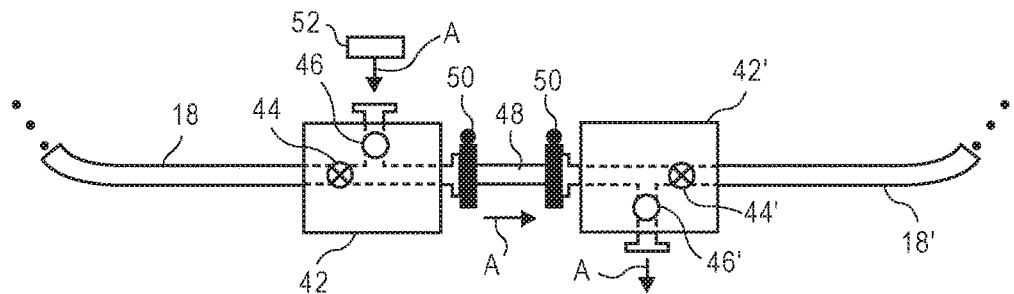
Figure 4D:
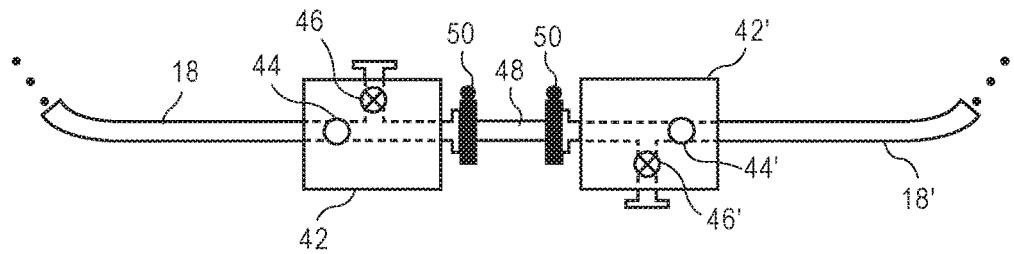
Figure 4E:
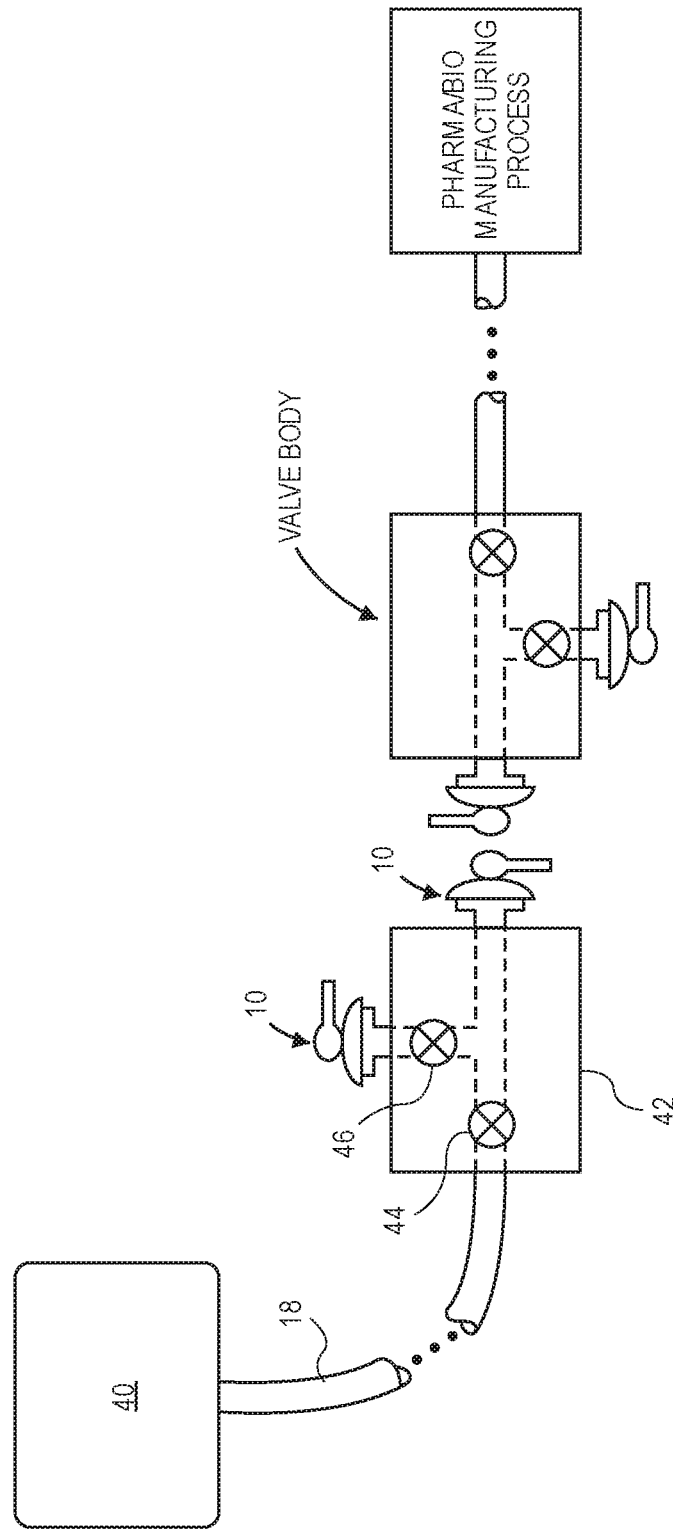

With reference to FIG. 4C, a sterilant 52 is then introduced into the pathway formed between the two branch conduits 18b, 18b' by opening valves 46, 46'. The sterilant 52 may include steam, a chemical agent, ozone, or the like. Arrows A in FIG. 4C illustrate the flow direction of the sterilant 52 although the direction may be reversed. After sufficient time has elapsed, the flow of sterilant 52 is stopped. As seen in FIG. 4D, the valves 46, 46' are then closed and the remaining valves 44, 44' are opened. A sterile or aseptic connection is now achieved. Fluid, reagents, products, and the like can now be transferred or fed from one location to another in an aseptic manner. The plugs 10, 10' were necessary to maintain component sterility prior to the connection being made. While FIGS. 4A-4D illustrate different bags or containers 40, 40' being connected, the same process may be used to connect one bag or container 40 to any other connection as part of the manufacturing process as is illustrated in FIG. 4E. For example, in many bio and pharmaceutical processes reagents or products may need to be swapped in or out of a manufacturing process. The process outlined in FIGS. 4A-4E can be used in another number of scenarios. The plugs 10, 10' that are used ensured component sterility and may be disposed of after use. In the configuration of FIGS. 4A-4E, the valve bodies 42, 42' are arranged in a block-and-bleed arrangement.

FIG. 5 illustrates one embodiment of a valve body 42 according to one embodiment. In this embodiment, there is a two-part valve body 42 (illustrated in the open configuration in FIG. 5) that includes a first half 42a and a second half 42b that are connected via a hinge 43. Each of the first half 42a and the second half 42b of the valve body 42 includes respective semi-circular shaped inner surface that defines a passageway through the valve body 42 when the valve body 42 is in the closed state. In this particular example, the semi-circular shaped inner surfaces define a tee-shaped passageway although different shaped passageways are contemplated. The semi-circular shaped inner surfaces combine to form a circular-shaped inner surface that snugly holds the circular shaped conduit 18.

Still referring to FIG. 5, the valve body 42 includes a fastener 54 that is used to maintain the valve body 42 in a closed state and can be used to selectively open the valve body 42 as needed. In this example, the fastener 54 includes a threaded latch 56 element that is pivotably held in the valve body half 42b and a knob 58 is used to tighten or loosen the latch 56 in place with respect to the second valve body half 42a that includes a notch for receiving the latch 56. The valve body 42 may be made from a number of materials. For example, the valve body 42 may be made of a metal such as stainless steel. Alternatively, the valve body 42 may be made from a polymer material such as acrylonitrile butadiene styrene (ABS) or other engineered thermoplastic materials suitable for the environment or application. Examples include polyetherimide (PEI), aliphatic polyamides (e.g., Nylon), polyphenylsulfone (e.g., RADEL), etc.

As seen in FIG. 5, the valve body 42 has terminating flanges 60, 62, 64 in which each half of the respective flange is formed respective halves 42a, 42b of the valve body 42. The flanges 60, 62, 64 are fully formed when the valve body 42 is in the closed state. Note that in some alternative embodiments, the valve body 42 may omit the terminating flanges 60, 62, 64. In the embodiment of FIG. 5, the valve body 42 is illustrated with two valves 44, 46 that are mounted on the valve body 42. Each valve 44, 46 includes an actuator element 66 that passes through an opening in the respective valve body half 42a, 42b and is selectively actuated to "pinch" an unreinforced polymer conduit 18 that is disposed inside the passageway of the valve body 42. The valves 44, 46 may be any number of types of valves commonly known to those skilled in the art. For example, the valves 44, 46 may be manual valves whereby a bonnet or the like is rotated manually to advance/retract the actuator 66. Alternatively, the valves 44, 46 may be automatically actuated valves. The valves 44, 46 illustrated in FIG. 5 are pneumatically actuated valves using air ports 68, 70. The valves 44, 46 illustrated in FIG. 5 also include an optional position feedback indication switch 72 that indicate the position of the valve 44, 46 (e.g., open or closed). The position feedback indication switch 72 may include a port 74 for electrical cabling.

Still referring to FIG. 5, the valve body 42 (in this embodiment) includes a two-part jacket 76 that includes a first half 76a and a second half 76b that encapsulates the portion of the conduit 18 that extends beyond the valve body 42. For example, the two-part jacket 76 may to cover the conduit segment 48 of FIGS. 4A-4D. The two-part jacket 76 is preferably made of a rigid construction using, for example, a polymer based material. Materials include standard thermoplastics and polyolefins such as polyethylene (PE) and polypropylene (PP) or a hard plastic such as polyetherimide (PEI) such as ULTEM resins. The two-part jacket 76 may also be formed from fluoropolymers such as polyvinylidene fluoride (PVDF) or perfluoroalkoxy (PFA), polytetrafluoroethylene (PTFE), polycarbonate (which may be more thermally resistant), polysulfone (PSU), and the like. The two halves 76a, 76b of the jacket 76 are connected via hinges 78 that allow the jacket 76 to be opened and closed as needed. The two-part jacket 78 defines an exoskeleton-type structure that surrounds the unreinforced polymer conduit 18 and prevents the unreinforced polymer conduit 18 from failing (e.g., bursting or forming an aneurysm type bulge in the conduit) under high fluid pressures.

In the embodiment of FIG. 5, the ends of the two-part jacket 76 includes flanges 80, 82 that are formed in each half 76a, 76b. In this embodiment, flange 80 is formed to mate with the flange 64 of the two-part valve body 42. An optional seal such as an o-ring type seal (not shown) may be placed between the flanges 80, 64 to aid in forming a fluid-tight seal. In this configuration, a conventional clamp such as clamp 50 of FIGS. 4B-4D may be positioned about the mated flanges 80, 64 to secure the two-part jacket 76 to the two-part valve body 42. Still referring to FIG. 5, the unreinforced polymer conduit 18 is illustrated disposed within the circular-shaped passageway formed in the two-part valve body 42 and the passageway formed in the two-part jacket 76. The unreinforced polymer conduit 18 may be made from a polymer thermoplastic elastomers (TPE), thermoplastic rubber (TPR), silicone (thermally or UV-cured), or other polymers.

In one aspect of the invention, the outer diameter of the unreinforced polymer conduit 18 is substantially equal to the inner diameters of the passageways in the valve body 42 and jacket 76. In this regard, both the two-part valve body 42 and the two-part jacket 76 snugly encapsulates the unreinforced polymer conduit 18 and provides resistance to expansion or other movement of the unreinforced polymer conduit 18 caused by high fluid pressures. As illustrated in FIG. 5, the ends of the unreinforced polymer conduit 18 include respective flanges 86, 88, 90 that are dimensioned to fit and reside within the corresponding flanges of the two-part valve body 42 and the flange of the two-part jacket 76. The flanges 86, 88, 90 may be constructed such that an adjacent flange from another unreinforced polymer conduit 18 (e.g., segment 48 in FIGS. 4A-4D) will mate to form a fluid-tight seal. For example, the flange 86, 88, 90 may contain a male sealing ring or extension that fits within a corresponding female recess of another unreinforced polymer conduit 18 (or vice versa). The dimensions of the unreinforced polymer conduit 18 may vary. The inner diameter of the unreinforced polymer conduit 18 may range from ⅛ inch up to 2.5 inches or more.

It should be understood that while many different embodiments are discussed herein, different embodiments may incorporate features or elements of other embodiments even though there are not specifically mentioned herein. For example, in FIG. 5, the two-part jacket 76 may be omitted or, alternatively, two valve bodies 42, 42' can be connected directly to one another (without any conduit segment 48) or with other types of jackets 76. Moreover, in some embodiments, there are no exposed portions of conduit 18, '18. Instead, the conduit 18, 18' is encapsulated within a jacket or other structure. Moreover, while the specific block-and-bleed valve arrangement of FIGS. 4A-4E is illustrated, the plugs 10, 10' may be used in any number of different configurations. In addition, while the plugs and other aspects described herein have largely been described in the context of pharmaceutical or biologic drug production processes, the plugs may also be used in other sterile processes (e.g., food or dairy production). While embodiments of the present invention have been shown and described, various modifications may be made without departing from the scope of the present invention. The invention, therefore, should not be limited, except to the following claims, and their equivalents.

What is claimed is:

1. A method of connecting a fluid container to a secondary conduit in a sterile manner comprising:
    sterilizing the fluid container and a first conduit connected to the fluid container, wherein the first conduit includes a main conduit and branch conduit and wherein an end of the branch conduit and an end of the main conduit each contain a removable plug therein;
    securing a first valve body around the main conduit and the branch conduit of the first conduit, wherein the first valve body includes a first valve for the main conduit and second valve for the branch conduit;
    closing the first valve of the first valve body and closing the second valve of the first valve body;
    removing the plugs from the branch conduit and main conduit of the first conduit;
    securing a second valve body around a secondary conduit, the secondary conduit having a main conduit and a branch conduit, wherein the second valve body includes a first valve for the main conduit and second valve for the branch conduit of the secondary conduit;
    fluidically connecting an output of the main conduit of the first conduit to the main conduit of the secondary conduit;
    opening the second valve of the first valve body and opening the second valve of the second valve body;
    flowing a sterilant through a fluid pathway connecting between the branch channel of the first conduit and the branch channel of the secondary conduit;
    closing the second valve of the first valve body and closing the second valve of the second valve body; and
    opening the first valve of the first valve body and opening the first valve of the second valve body.

2. The method of claim 1, wherein the first valve body comprises a first half and a second half hinged with respect to one another, wherein the main conduit and the branch conduit of the first conduit is disposed between the first half and the second half.

3. The method of claim 1, wherein prior to securing the output of the main conduit of the first conduit to the main conduit of the secondary conduit comprises closing the first valve of the second valve body and the second valve of the second valve body and removing plugs from the main conduit and the branch conduit of the secondary conduit.

4. The method of claim 1, wherein the fluid container comprises a bag.

5. The method of claim 1, wherein sterilizing comprises irradiating the fluid container, first conduit, and plugs with gamma irradiation.

6. The method of claim 1, wherein the sterilant comprises steam, a chemical agent, or ozone.

7. The method of claim 1, wherein the removable plugs each comprise:
   a cap;
   a shank portion extending from the cap;
   a flexible ring disposed along a portion of the shank; and
   a lever mounted on the cap and configured to shorten the shank upon actuation, wherein actuation of the lever causes radial expansion of the flexible ring and forms a fluidic seal with an interior surface of the flexible polymer conduit, wherein the removable plug is formed form a polymer material that tolerates gamma radiation.

* * * * *